US00PP36036P2

(12) United States Plant Patent
Hattori

(10) Patent No.: US PP36,036 P2
(45) Date of Patent: Jul. 23, 2024

(54) ***HELLEBORUS* PLANT NAMED 'HOLLOWTOP MOUNTAIN'**

(50) Latin Name: *Helleborus niger*
Varietal Denomination: Hollowtop Mountain

(71) Applicant: Miyoko Hattori, Tokyo (JP)

(72) Inventor: Miyoko Hattori, Tokyo (JP)

( * ) Notice: Subject to any disclaimer, the term of this patent is extended or adjusted under 35 U.S.C. 154(b) by 0 days.

(21) Appl. No.: 18/235,833

(22) Filed: Aug. 19, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. Anne Whealy

(57) ABSTRACT

A new and distinct cultivar of *Helleborus* plant named 'Hollowtop Mountain', characterized by its compact, upright to somewhat outwardly spreading and mounding plant habit; moderately vigorous growth habit; medium green-colored leaflets with distinctive light grey-colored centers and venation and dark red-colored petioles; freely flowering habit; white-colored flowers that are held above the foliar plane on dark red-colored peduncles; and good garden performance.

1 Drawing Sheet

Botanical designation: *Helleborus niger.*
Cultivar denomination: 'HOLLOWTOP MOUNTAIN'.

BACKGROUND OF THE INVENTION

The present invention relates to a new and distinct cultivar of *Helleborus* plant, botanically known as *Helleborus niger* and hereinafter referred to by the name 'Hollowtop Mountain'.

The new *Helleborus* plant is a product of a planned breeding program conducted by the Inventor in Tokyo, Japan. The objective of the breeding program was to create new vigorous and freely-flowering *Helleborus* plants with marbled leaflets, rapid growth rate and attractive flowers.

The new *Helleborus* plant originated from a cross-pollination conducted by the Inventor in Toyko, Japan in March, 2003 of a proprietary selection of *Helleborus niger* identified as code "A", as the female, or seed, parent, not patented, with a proprietary selection of *Helleborus niger* identified as code "B" as the male, or pollen, parent, not patented. The new *Helleborus* plant was discovered and selected by the Inventor as a single flowering plant from within the progeny of the stated cross-pollination grown in a controlled greenhouse environment in Tokyo, Japan in March, 2010.

Asexual reproduction of the new *Helleborus* plant by divisions in a controlled greenhouse environment in Tokyo, Japan since March, 2010, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'Hollowtop Mountain'. These characteristics in combination distinguish 'Hollowtop Mountain' as a new and distinct *Helleborus* plant:

1. Compact, upright to somewhat outwardly spreading and mounding plant habit.
2. Moderately vigorous growth habit.
3. Medium green-colored leaflets with distinctive light grey-colored centers and venation and dark red-colored petioles.
4. Freely flowering habit.
5. White-colored flowers that are held above the foliar plane on dark red-colored peduncles.
6. Good garden performance.

Plants of the new *Helleborus* differ primarily from plants of the female and male parent selections in leaflet color as leaflets of plants of the new *Helleborus* are medium green in color with distinctive light grey-colored centers and venation whereas leaflets of plants of the parent selections are solid green in color.

Plants of the new *Helleborus* can be compared to plants of *Helleborus niger* 'COSEH 220', disclosed in U.S. Plant Pat. No. 21,092. In side-by-side comparisons, plants of the new *Helleborus* differ from plants of 'COSEH 220' in the following characteristics:

1. Plants of the new *Helleborus* have larger leaflets than plants of 'COSEH 220'.
2. Leaflets of plants of the new *Helleborus* are medium green in color with distinctive light grey-colored centers and venation whereas leaflets of plants of 'COSEH 200' are solid green in color.
3. Petioles of plants of the new *Helleborus* are dark red in color whereas petioles of plants of 'COSEH 220' are green to reddish brown in color.

4. Plants of the new *Helleborus* flower earlier than plants of 'COSEH 220'.
5. Plants of the new *Helleborus* have shorter peduncles than plants of 'COSEH 220'.
6. Peduncles of plants of the new *Helleborus* are dark red in color whereas peduncles of plants of 'COSEH 220' are green in color with random dark red-colored spots.
7. Flowers of plants of the new *Helleborus* have fewer stamens and fewer nectaries than plants of 'COSEH 220'.

Plants of the new *Helleborus* can also be compared to plants of *Helleborus niger* 'COSEH210', disclosed in U.S. Plant Pat. No. 21,048. In side-by-side comparisons, plants of the new *Helleborus* differ from plants of 'COSEH210' in the following characteristics:

1. Leaflets of plants of the new *Helleborus* are medium green in color with distinctive light grey-colored centers and venation whereas leaflets of plants of 'COSEH210' are solid green in color.
2. Petioles of plants of the new *Helleborus* are dark red in color whereas petioles of plants of 'COSEH210' are green to reddish brown in color.
3. Plants of the new *Helleborus* flower earlier than plants of 'COSEH210'.

BRIEF DESCRIPTION OF THE PHOTOGRAPH

The accompanying colored photograph illustrates the overall appearance of the new *Helleborus* plant showing the colors as true as it is reasonably possible to obtain in colored reproductions of this type. Colors in the photograph may differ slightly from the color values cited in the detailed botanical description which accurately describe the colors of the new *Helleborus* plant. The photograph is a side perspective view of a typical flowering plant of 'Hollowtop Mountain' grown in an outdoor nursery.

DETAILED BOTANICAL DESCRIPTION

The aforementioned photograph and following observations, measurements and values describe plants grown during the winter and early spring in an outdoor nursery in Smoketown, Pennsylvania and under cultural practices typical of commercial *Helleborus* production. During the production of the plants, day temperatures ranged from 7 C to 11 C, night temperatures ranged from −1 C to 1.5 C and light levels ranged from 30 to 70 Klux. Plants were 1.75 years old when the photograph and the description were taken. In the following description, color references are made to The Royal Horticultural Society Colour Chart, Sixth Edition, except where general terms of ordinary dictionary significance are used.

Botanical classification: *Helleborus niger* 'Hollowtop Mountain'.

Parentage:

*Female, or seed, parent*.—Proprietary selection of *Helleborus niger* identified as code "A", not patented.

*Male, or pollen, parent*.—Proprietary selection of *Helleborus niger* identified as code "B", not patented.

Propagation:

*Type*.—By meristem culture.

*Time to initiate roots*.—About three to four weeks at soil temperatures about 21 C to 22 C.

*Time to produce a rooted young plant*.—About six to eight weeks at soil temperatures about 21 C to 22 C.

*Root description*.—Fleshy, medium in thickness; typically brown to white in color, actual color of the roots is dependent on substrate composition, water quality, fertilizer type and formulation, substrate temperature and physiological age of roots.

*Rooting habit*.—Moderate branching; medium density.

Plant description:

*Plant and growth habit*.—Herbaceous perennial; compact, upright to somewhat outwardly spreading and mounding plant habit; moderately vigorous growth habit and moderate growth rate; leaves arranged in basal rosettes.

*Plant height, soil level to top of foliar plane*.—About 14 cm.

*Plant height, soil level to top of floral plane*.—About 16 cm.

*Plant diameter* (*area of spread*).—About 35 cm.

Leaf description:

*Arrangement*.—Leaves arranged alternately in a basal rosette; leaves palmately compound with typically seven leaflets per leaf.

*Leaflet length*.—About 10 cm to 14 cm.

*Leaflet width*.—About 3 cm to 5 cm.

*Leaflet shape*.—Elliptic.

*Leaflet apex*.—Acute.

*Leaflet base*.—Attenuate.

*Leaflet margin*.—Serrate; at maturity, undulate.

*Leaflet texture and luster, upper and lower surfaces*.—Smooth, glabrous; leathery; slightly glossy.

*Leaflet venation pattern*.—Pinnate and reticulate.

*Leaflet color*.—Developing leaflets, upper surface: Close to 146A; center and midvein, marbled with close to 155A; midvein at the petiole, close to 59A. Developing leaflets, lower surface: Close to 146B; midvein at the petiole, close to 59A. Fully expanded leaflets, upper surface: Close to 146B; center and midvein, marbled with close to 191C; midvein at the petiole, close to 160A and at the apex, close to 3A. Fully expanded leaflets, lower surface: Close to 147B; midvein, close to 59A.

*Petioles*.—Length, fully expanded leaflets: About 10 cm. Diameter, fully expanded leaflets: About 4 mm to 5 mm. Strength: Strong. Texture, upper and lower surfaces: Smooth, glabrous. Color, upper and lower surfaces: Close to 144C heavily covered with fine dots, close to 59A.

Flower description:

*Flower shape and habit*.—Single rotate flowers that are slightly bowl-shaped; freely flowering habit with typically about 20 flowers developing per plant; flowers face outwardly to nodding.

*Fragrance*.—Moderately fragrant, pleasant.

*Natural flowering season*.—Plants initially flower in early November and after cold temperatures subside, will reflower from February into May in Pennsylvania.

*Flower longevity on the plant*.—About three weeks; sepals are persistent and other flower parts are not persistent.

*Flower buds*.—Length: About 2 cm. Diameter: About 1 cm. Shape: Ovoid. Texture and luster: Smooth, glabrous; matte to pearly. Color: Close to 2D.

*Flower diameter*.—About 6 cm to 8 cm.

*Flower depth* (*height*).—About 4 cm.

*Petals*.—None observed; transformed into nectaries.

*Sepals*.—Quantity and arrangement: Five arranged in a single whorl. Length: About 5 cm. Width: About 3.5 cm. Shape: Broadly ovate and slightly concave. Apex: Obtuse. Base: Obtuse. Margin: Entire. Texture and luster, upper and lower surfaces: Smooth, glabrous; satiny and pearly. Color: When opening, upper and lower surfaces: Close to 155A. Fully opened, upper surface: Close to 155D. Fully opened, lower surface: Close to 155B.

*Flower bracts*.—Quantity and arrangement: About one or two at the base of the flower. Length: About 3 cm to 4 cm. Width: About 5 mm to 12 mm. Shape: Lanceolate. Apex: Acute. Base: Attenuate. Margin: Mostly entire; at the apex, slightly serrate. Texture and luster, upper and lower surfaces: Smooth, glabrous; waxy; matte. Color: When opening, upper and lower surfaces: Close to 146B to 146C. Fully opened, upper and lower surfaces: Close to 146B to 146C.

*Peduncles*.—Length: About 10 cm. Diameter: About 3 mm. Strength: Moderately strong; flexible. Aspect: Mostly upright. Texture and luster: Smooth, glabrous; slightly glossy. Color: Close to 144C heavily covered with fine dots, close to 59A.

*Reproductive organs*.—Stamens: Quantity per flower: About 50. Filament length: About 1.6 cm. Filament color: Close to NN155D. Anther shape: Elliptical. Anther size: About 1 mm by 2 mm. Anther color: Close to NN155D. Pollen amount: If present, scarce. Pollen color: Close to 2C. Pistils: Quantity per flower: About eight. Pistil length: About 1.7 cm. Stigma shape: Tapered, pointed. Stigma color: Close to 183A. Style length: About 1 cm. Style color: Close to 1B. Ovary color: Close to 1B.

*Nectaries*.—Quantity per flower: About 12 to 15. Length: About 8 mm. Width: Proximally, close to 1 mm and distally, close to 4 mm. Shape: Salverform. Apex: Rounded. Margin: Entire. Texture and luster: Mostly smooth and glabrous; at the margins, sparsely hirsutulous. Color: Proximally, close to 7A and distally, close to 7D.

*Seeds and fruits*.—To date, seed and fruit development have not been observed on plants of the new *Helleborus*.

Garden performance: Plants of the new *Helleborus* have been observed to have good garden performance and to tolerate rain, wind and temperatures ranging from about −15 C to about 34 C.

Pathogen & pest resistance: To date, plants of the new *Helleborus* have not been observed to be resistant to pathogens and pests common to *Helleborus* plants.

It is claimed:

1. A new and distinct *Helleborus* plant named 'Hollowtop Mountain' as illustrated and described.

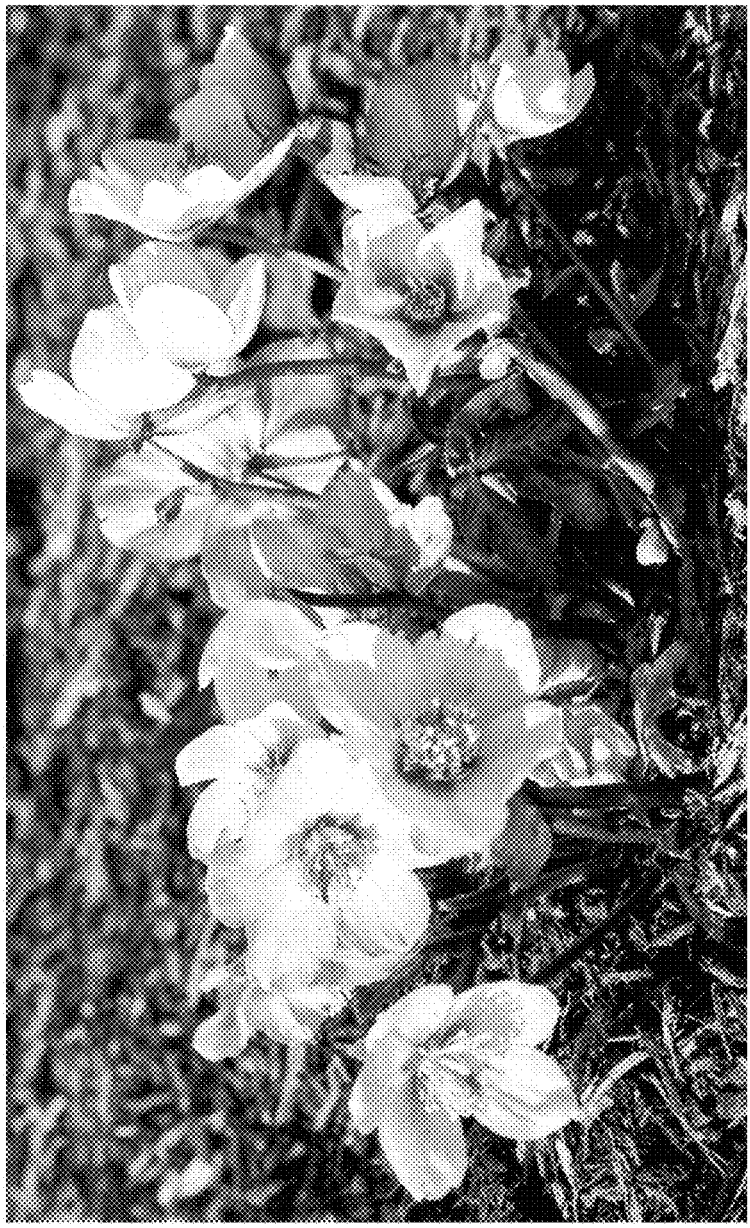

* * * * *